United States Patent [19]

Couture-Dorschner et al.

[11] Patent Number: 5,401,267

[45] Date of Patent: Mar. 28, 1995

[54] ABSORBENT ARTICLE HAVING ENHANCED WICKING CAPACITY

[75] Inventors: Laurie Couture-Dorschner, Hortonville; Valerie V. Finch, Neenah; Thomas H. Gilman, Appleton; David R. King, Neenah; Ann M. Nichols, Appleton, all of Wis.

[73] Assignee: Kimberly-Clark Corporation, Neenah, Wis.

[21] Appl. No.: 263,178

[22] Filed: Jun. 21, 1994

Related U.S. Application Data

[63] Continuation of Ser. No. 58,247, May 12, 1993, abandoned.

[51] Int. Cl.[6] ................... A61F 13/15; A61F 13/20
[52] U.S. Cl. ........................ 604/384; 604/358; 604/361; 604/378; 604/385.1; 604/386; 604/387; 604/389
[58] Field of Search ................ 604/358, 361–362, 604/378–384, 385.1, 386, 387, 389, 390

[56] References Cited

U.S. PATENT DOCUMENTS

| | | |
|---|---|---|
| 1,333,081 | 1/1920 | Otto . |
| 1,863,333 | 12/1929 | Heitmeyer . |
| 1,910,872 | 5/1933 | Williams . |
| 2,047,054 | 7/1936 | Beyer, Jr. et al. . |
| 2,564,689 | 8/1951 | Harwood et al. . |
| 2,772,678 | 12/1956 | Leupold . |
| 2,787,271 | 4/1957 | Clark . |
| 2,900,980 | 8/1959 | Harwood . |
| 3,073,308 | 1/1963 | Stamberger . |
| 3,088,463 | 5/1963 | Harmon . |
| 3,344,789 | 10/1967 | Arnold et al. . |
| 3,343,543 | 9/1967 | Glassman . |
| 3,375,827 | 4/1968 | Bletzinger et al. . |
| 3,397,697 | 8/1968 | Rickard . |
| 3,403,681 | 10/1968 | Hoey et al. . |
| 3,525,337 | 8/1970 | Simons et al. . |
| 3,545,442 | 12/1970 | Wicker . |
| 3,654,060 | 4/1972 | Goldman . |
| 3,654,929 | 4/1972 | Nilsson et al. . |
| 3,667,668 | 6/1972 | Nystrand et al. . |
| 3,686,941 | 8/1972 | Duane et al. . |
| 3,699,966 | 10/1972 | Chapuis . |
| 3,746,592 | 7/1973 | Nystrand et al. . |
| 3,771,525 | 11/1973 | Chapuis . |
| 3,865,112 | 2/1975 | Roeder . |
| 3,886,941 | 6/1975 | Duane et al. . |
| 3,929,135 | 12/1975 | Thompson . |
| 3,939,838 | 2/1976 | Fujinami et al. . |
| 3,945,386 | 3/1976 | Anczurowski et al. . |
| 3,954,107 | 5/1976 | Chesky et al. . |
| 3,965,906 | 6/1976 | Karami . |
| 3,967,623 | 7/1976 | Butterworth et al. . |

(List continued on next page.)

FOREIGN PATENT DOCUMENTS

0272683A2  6/1988  European Pat. Off. .
0298348A1  1/1989  European Pat. Off. .

(List continued on next page.)

Primary Examiner—Randall L. Green
Assistant Examiner—P. Zuttarelli
Attorney, Agent, or Firm—Thomas J. Connelly

[57] ABSTRACT

An absorbent article is disclosed which exhibits enhanced wicking capacity. The absorbent article includes a liquid-permeable cover, a liquid-impermeable baffle and an absorbent enclosed therebetween. The absorbent is constructed of first, second and third members. Each member has a wicking capacity for body fluids discharged by a human body. The first member has a high wicking capacity, the second member has a lower wicking capacity than the first member, and the third member has a greater wicking capacity than the second member. The different wicking capacities of the three members promotes a systematic distribution of body fluid away from the body-side cover down into the absorbent article. The second member also has an equal or greater width than either the first or third members so as to provide a visual cue of when the absorbent article is in need of changing. By changing the absorbent article when the second member appears to be soiled, the user can prevent side leakage and soiling of an adjacent undergarment.

37 Claims, 6 Drawing Sheets

U.S. PATENT DOCUMENTS

| | | |
|---|---|---|
| 3,994,299 | 11/1976 | Karami . |
| 4,014,341 | 3/1977 | Karami . |
| 4,029,101 | 6/1977 | Chesky et al. . |
| 4,037,602 | 7/1977 | Hawthorne ................... 604/385.1 |
| 4,057,061 | 11/1977 | Ishikawa et al. . |
| 4,069,822 | 1/1978 | Buell . |
| 4,079,739 | 3/1978 | Whitehead . |
| 4,100,324 | 7/1978 | Anderson et al. . |
| 4,195,634 | 4/1980 | DiSalvo et al. ................ 604/385.1 |
| 4,223,677 | 9/1980 | Anderson . |
| 4,232,674 | 11/1980 | Melican . |
| 4,285,343 | 8/1981 | McNair . |
| 4,323,068 | 4/1982 | Aziz . |
| 4,323,069 | 4/1982 | Ahr et al. . |
| 4,324,246 | 4/1982 | Mullane et al. . |
| 4,327,731 | 5/1982 | Powell . |
| 4,357,939 | 11/1982 | Jackson et al. . |
| 4,372,312 | 2/1983 | Fendler et al. . |
| 4,397,644 | 8/1983 | Matthews et al. . |
| 4,411,660 | 10/1983 | Dawn et al. ....................... 604/378 |
| 4,433,972 | 2/1984 | Malfitano . |
| 4,507,121 | 3/1985 | Leung . |
| 4,540,414 | 9/1985 | Wishman . |
| 4,551,142 | 11/1985 | Kopolow . |
| 4,589,876 | 5/1986 | Van Tilburg . |
| 4,608,047 | 8/1986 | Mattingly . |
| 4,623,340 | 11/1986 | Luceri . |
| 4,626,254 | 12/1986 | Widlund et al. . |
| 4,627,848 | 12/1986 | Lassen et al. . |
| 4,629,643 | 12/1986 | Curro et al. . |
| 4,631,062 | 12/1986 | Lassen et al. . |
| 4,636,209 | 1/1987 | Lassen . |
| 4,676,786 | 6/1987 | Nishino ........................... 604/385.1 |
| 4,687,478 | 8/1987 | Van Tilburg . |
| 4,690,679 | 9/1987 | Mattingly, III et al. . |
| 4,705,513 | 11/1987 | Sheldon et al. ....................... 604/361 |
| 4,710,186 | 12/1987 | DeRossett et al. . |
| 4,731,071 | 3/1988 | Pigneul . |
| 4,738,674 | 4/1988 | Todd et al. . |
| 4,741,941 | 5/1988 | Englebert et al. . |
| 4,755,413 | 7/1988 | Morris . |
| 4,773,905 | 9/1988 | Molee et al. . |
| 4,798,601 | 1/1989 | Shirose et al. . |
| 4,798,603 | 1/1989 | Meyer et al. . |
| 4,798,604 | 1/1989 | Carter . |
| 4,806,411 | 2/1989 | Mattingly, III et al. . |
| 4,822,668 | 4/1989 | Tanaka et al. . |
| 4,846,813 | 7/1989 | Raley . |
| 4,846,824 | 7/1989 | Lassen et al. . |
| 4,880,419 | 11/1989 | Ness . |
| 4,886,632 | 12/1989 | Van Iten et al. . |
| 4,892,534 | 1/1990 | Datta et al. . |
| 4,895,749 | 1/1990 | Rose . |
| 4,908,026 | 3/1990 | Suniennik et al. . |
| 4,950,264 | 8/1990 | Osborn, III . |
| 4,963,139 | 10/1990 | Dabroski ........................... 604/385.1 |
| 4,973,325 | 11/1990 | Sherrod et al. . |
| 4,988,344 | 1/1991 | Reising et al. . |
| 5,009,653 | 4/1991 | Osborn, III . |
| 5,037,409 | 8/1991 | Chen et al. . |
| 5,037,412 | 8/1991 | Tanzer et al. . |
| 5,125,918 | 6/1992 | Seidy ................................... 604/386 |
| 5,135,521 | 8/1992 | Luceri et al. . |
| 5,188,625 | 4/1993 | Van Iten et al. . |
| 5,201,727 | 4/1993 | Nakanishi et al. . |
| 5,219,341 | 6/1993 | Serbiak et al. . |
| 5,257,982 | 11/1993 | Cohen . |
| 5,348,547 | 9/1994 | Payne et al. ........................ 604/378 |

FOREIGN PATENT DOCUMENTS

| | | |
|---|---|---|
| 0316771A3 | 5/1989 | European Pat. Off. . |
| 0401189A1 | 12/1990 | European Pat. Off. . |
| 0471114A3 | 2/1992 | European Pat. Off. . |
| 0234194B1 | 11/1992 | European Pat. Off. . |
| 0548714A2 | 6/1993 | European Pat. Off. . |
| 122727 | 8/1989 | Japan . |
| 168950 | 6/1990 | Japan . |
| 59526 | 2/1993 | Japan . |
| 59529 | 2/1993 | Japan . |
| 1333081 | 10/1973 | United Kingdom . |
| 2124907 | 2/1984 | United Kingdom . |
| 2165757 | 4/1986 | United Kingdom . |
| 2168612 | 6/1986 | United Kingdom . |
| 2180162 | 3/1987 | United Kingdom . |
| 2258403 | 2/1993 | United Kingdom . |
| 2258840 | 2/1993 | United Kingdom . |
| 9100719 | 1/1991 | WIPO ................................. 604/378 |
| WO91/11163 | 8/1991 | WIPO . |
| WO91/14415 | 10/1991 | WIPO . |
| WO93/01780 | 2/1993 | WIPO . |

ABSORBENT ARTICLE HAVING ENHANCED WICKING CAPACITY

This is a continuation of application Ser. No. 08/058,247, filed on May 12, 1993, now abandoned.

FIELD OF THE INVENTION

This invention relates to an absorbent article for absorbing body fluid especially menses and blood. More particularly, this invention relates to an absorbent article having an absorbent which is constructed of three members, each having a predetermined wicking capacity.

BACKGROUND OF THE INVENTION

An absorbent article refers to products such as diapers, sanitary napkins, training pants, incontinent garments, overnight pads, panty liners, underarm shields, and the like which are used to absorb body fluid, such as urine, menses, blood, perspiration, and other excrements discharged by a body. Sanitary napkins, also referred to as catamenial pads, feminine pads, overnight pads, panty liners and panty shields are designed to be worn by a female to absorb menses and other body fluids discharged before, during and after a menstrual period. Such products are external devices which are generally held in position by a garment attachment adhesive or by a mechanical attachment to an adjacent undergarment. Such products differ from tampons which are classified as internal devices and which are designed to be physically inserted into a woman's vagina.

Functionally, sanitary napkins and overnight pads differ from panty liners and panty shields in that they are generally constructed to absorb a greater quantity of body fluid and are designed to be worn for a longer period of time.

In order to adequately perform their function, modern catamenial products are constructed of highly absorbent materials. However, if any absorbent material is utilized up to the point where it becomes fully saturated, there is a possibility that leakage of body fluid could occur. Such leakage could stain the user's clothing. Many times, leakage occurs before the absorbent is near its maximum absorbent capacity because only a small portion of the absorbent is utilized. It is therefore, desirable to construct, an absorbent article which has the capacity to rapidly wick the fluid to a large portion of the absorbent so as to prevent premature side leakage.

It is also desirable to construct an absorbent article which can supply an in-use visual signal to the user that the body fluid which entered the article will stay in the center thereof. A post-use visual signal is also beneficial in letting the user know that the fluid has remained in the center of the absorbent article thereby reinforcing the in-use visual signal. The post-use visual signal also lets the user know that the article may be approaching it's saturation limit and that it may be time to change the article.

Therefore, there is a need to provide an absorbent article which can rapidly wick fluid throughout the absorbent and which can provide the user with a post-use visual signal to determine if it is near its absorption limits. If the absorbent article is close to its limit, the user could then replace the product before leakage occurs.

Another important aspect of a catamenial product is its ability to wick menses. Menses is very viscous and can contain small particles of body tissue which tend to cling to the cover and can restrict the passage of additional body fluid into the absorbent article. Manufacturers of sanitary napkins are always on the lookout for a new material or a synergistic effect of rearranging known materials to obtain a structure which has improved wicking capacities.

Now an absorbent article has been invented which has rapid wicking capacity within the absorbent, as well as providing both an in-use visual signal showing that the fluid will stay in the center of the article and a post-use visual signal indicating when the article is approaching it's saturation limit.

SUMMARY OF THE INVENTION

Briefly, this invention relates to an absorbent article having an absorbent constructed of first, second and third members. Each member has a wicking capacity for menses, blood and other fluids discharged by a human body. The first member has a high wicking capacity and provides an in-use visual signal showing that the fluid will stay in the center of the article. The second member has a lower wicking capacity than the first member, and the third member has a greater wicking capacity than the second member. The different wicking capacities of the three members promotes a systematic distribution of body fluid away from the bodyside cover down into the absorbent article. The second member also has an equal or greater width than either the first or third members so as to provide a post-use visual signal indicating when the article is approaching it's saturation limit. By changing the absorbent article when the second member appears to be soiled, the user can prevent side leakage and soiling of an adjacent undergarment. The second member also has a basis weight of less than about 300 grams per square meter (gsm) so that the user can visually observe that the fluid is being pulled into the third member.

The general object of this invention is to provide an absorbent article for absorbing body fluids, especially menses and blood. A more specific object of this invention is to provide an absorbent article, such as a sanitary napkin, which provides both an in-use and a post-use visual signal to the user.

Another object of this invention is to provide a thin absorbent article having a thickness of less than 15 millimeters and which has a high level of comfort while providing rapid fluid intake.

Still another object of this invention is to provide an absorbent article which exhibits enhanced wicking and control of body fluid within the absorbent article.

A further object of this invention is to provide an absorbent article, such as a sanitary napkin or a panty liner, which provides a post-use visual signal to the user indicating when the article is approaching it's saturation limit.

Still another object of this invention is to provide an absorbent article which has a line of flexure which allows the article to conform and stay in intimate contact with the user's body.

Other objects and advantages of the present invention will become more apparent to those skilled in the art in view of the following description and the accompanying drawings.

DETAILED DESCRIPTION OF THE PREFERRED EMBODIMENT

Figure 1:
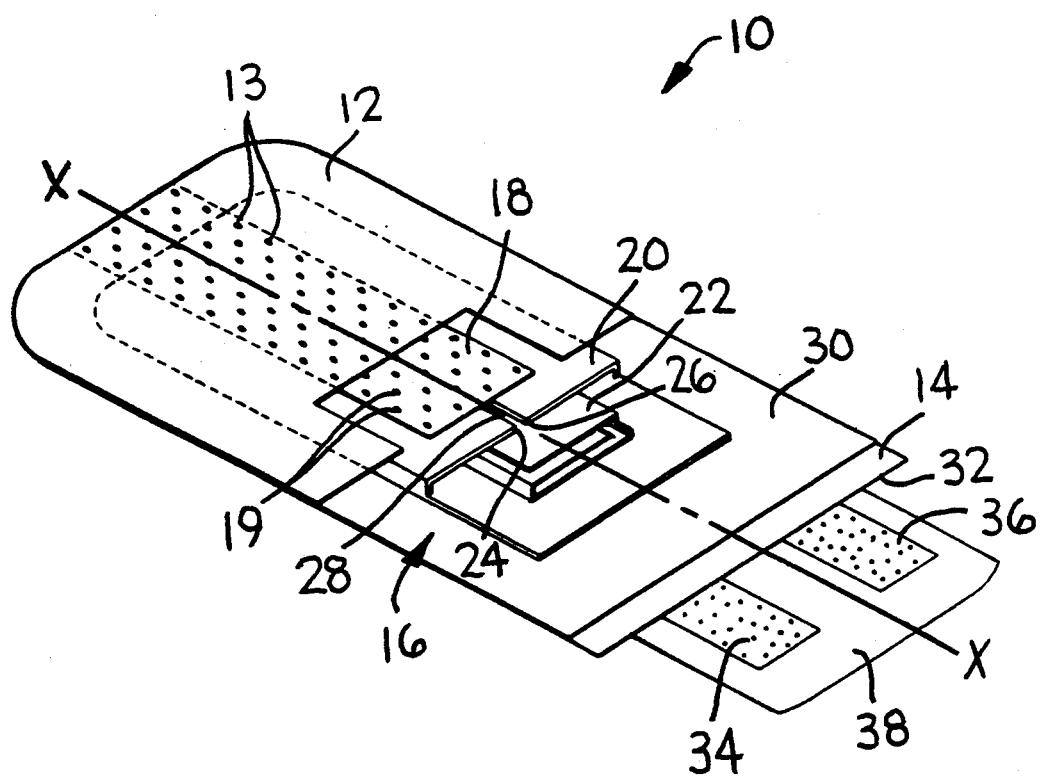
FIG. 1 is a cut away, perspective view of an absorbent article, having an absorbent constructed of three members having predetermined wicking capacities and wherein the third member is positioned within the second member.

Referring to FIG. 1, an absorbent article 10 is shown which is capable of absorbing body fluid. The absorbent article can be a diaper, a training pant, a sanitary napkin, a panty liner, an overnight pad, an incontinent garment, an underarm shield or any other known disposable product capable of absorbing urine, menses, blood, perspiration, excrement or other fluid discharged by a human body. For purpose of discussion, the absorbent article 10 will be described in terms of a sanitary napkin.

The absorbent article 10 includes a liquid-permeable cover 12, a liquid-impermeable baffle 14 and an absorbent 16 enclosed therebetween. The liquid-permeable cover 12 is designed to contact the body of the user and can be constructed of a woven or nonwoven material. The cover 12 can be constructed from natural or synthetic materials and should be easily penetrated by body fluid. Suitable materials include bonded carded webs of polyester, polypropylene, polyethylene, nylon or other heat-bondable fibers. Other polyolefins, such as copolymers of polypropylene and polyethylene, linear low-density polyethylene, finely-perforated film webs and net material, also work well. The cover 12 can also be constructed of a thermoplastic film which contains apertures and is flanked on both sides by a nonwoven material. This particular embodiment provides a soft feel against the user's thighs while allowing body fluid to rapidly pass therethrough.

In order to facilitate movement of body fluid down into the absorbent article 10, one could form a plurality of apertures 13 in the cover 12. The apertures 13 can be randomly or uniformly arranged throughout the cover 12, or they can be located only in a narrow longitudinal band or strip arranged along the longitudinal axis X—X of the absorbent article 10. The apertures 13 permit rapid penetration of the body fluid down into the absorbent 16. The size, shape, diameter and number of apertures can vary to suit one's particular needs.

The liquid-impermeable baffle 14 is designed to permit the passage of air or vapor out of the absorbent article 10 while blocking the passage of liquids. The baffle 14 can be made from any material having the above-identified properties. A good material is a microembossed, polymeric film, such as polyethylene or polypropylene. Bi-component films can also be used. A preferred material is polyethylene film. Most preferably, the baffle 14 will be a polyethylene film having a thickness in the range of about 0.2 to about 2.0 millimeters (mm), preferably about 0.3–1.0 mm.

The cover 12 and the baffle 14 can be coextensive and in face to face contact around the periphery of the absorbent 16. The cover 12 and the baffle 14 can be sealed together about their peripheries by use of an adhesive, by heat sealing, by ultrasonics, or by any other process known to those in the art.

The absorbent 16 consists of at least three separate and distinct members 18, 20 and 22, each having a predetermined wicking capacity. The first member 18 is positioned immediately below the cover 12 and is aligned along the central longitudinal axis X—X of the absorbent article 10. The first member 18 provides an in-use visual signal to the user that the body fluid in the center of the absorbent article. The first member 18 can also have a high wicking capacity, especially for menses, and can be comprised of a fine pore, highly pigmented fabric. The first member 18 is of a different color, and preferably darker, than the cover 12 and/or the second member 20. Peach, pink or blue offers a good an in-use visual signal that the fluid will stay in the center of the absorbent article 10. The first member 18 can alternatively be a coating or layer of ink deposited on a surface of the cover 12 or on a surface of the second member 20. For the purpose of discussion, the first member 18 will be described as an absorbent member having wicking properties.

Meltblown works well for the first member 18, for it has excellent menses distribution properties. A description of meltblown is taught in U.S. Pat. No. 4,798,603 issued to Meyer et al. and assigned to the present assignee. This patent is incorporated by reference and made a part hereof.

The first member 18 can be in the shape of a rectangular strip, having a length equal to or less than the overall length of the absorbent article 10, and a width less than the width of the absorbent article 10. A length of between about 6 to about 12 inches (about 152 to about 304 mm) and a width of between about 0.5 to about 2 inches (about 12 to about 25.4 mm) works well. Preferably, the first member 18 has a length approximately equal to the length of the absorbent article 10, and a width of between about 1 to about 1.5 inches (about 25.4 mm to about 38.1 mm), most preferably about 1.25 inches (about 31.75 mm).

The first member 18 should be capable of controlling the longitudinal and transverse movement of the body fluid which is delivered to the cover 12. Since the first member 18 is narrower than the absorbent article 10, the sides of the first member 18 are spaced away from the longitudinal side edges of the absorbent article 10, and the body fluid is restricted to the area within the periphery of the first member 18, before it passes down into the second member 20. This design enables the body fluid to be confined to the central area of the absorbent article 10, and to be wicked lengthwise so that a greater quantity of the second member 20 can be utilized.

In order to facilitate movement of body fluid down into the absorbent article 10, one could form a plurality of apertures 19 in the first member 18. Some or all of the apertures 13 formed in the cover 12 and the apertures 19 formed through the first member 18 can be axially aligned so as to rapidly allow the body fluid to penetrate down into the absorbent 16. The size, shape, diameter and number of apertures 19 can vary to suit one's particular needs. The apertures 19 can be uniformly or randomly arranged throughout all or a portion of the upper surface of the first member 18.

The second member 20 is positioned below the first member 18 and has a lower wicking capacity, especially for menses, than the first member 18 when the first member 18 is an absorbent having wicking properties. The second member 20 can have a length of between about 6 to about 12 inches (about 152 to about 304 mm). Preferably, the first member 18 has a length approximately equal to the length of the absorbent article 10. The second member 20 can be equal in width to the first member 18 but preferably will be wider. The width of the second member 20 can be between about 2 to about 3 inches (about 50.8 to about 76.2 mm), preferably about 2.5 inches (about 63.5 mm). A width greater than about 3 inches (about 50.8 mm) can cause discomfort to some users.

The second member 20 can be a hydrophilic material formed from various types of natural or synthetic fibers, including cellulose fibers, surfactant treated meltblown fibers, wood pulp fibers, regenerated cellulose or cotton fibers, or a blend of pulp and other fibers. Preferably, the second member 20 is formed from a material having a large pore structure and exhibits both wet and dry resiliency to ensure comfort and protection. Coform and air-laid fabric are two materials that work well as the second member. Coform is an air-formed blend of meltblown fibers and pulp fibers. The formation of such material is disclosed in U.S. Pat. No. 4,100,324 which issued to Anderson et al. This patent is incorporated by reference and made a part hereof. A coform mixture of about 60 percent cellulose fibers with about 40 percent polypropylene meltblown fibers, works well.

An air-laid fabric also works well for the second member 20. A commercially available air-laid fabric is Airtex® 395 sold by James River Corporation located at 500 Day St., P.O. Box 23790, Green Bay, Wisc. 54309-3790. Airtex® 395 is 100% virgin softwood held together by an acrylic binder.

The second member 20 can also contain thermoplastic polymers which can be permanently deformed by the application of heat and pressure. Such materials include polypropylene, nylon, polyethylene, polyesters, etc. Typical of such materials are bonded carded webs, spunbond fabrics, air-laid fabrics with thermally fusable binder fibers.

As shown in FIG. 1, the second member 20 is C-folded and has two oppositely aligned, longitudinal edges 24 and 26 which are spaced apart, preferably forming a longitudinal gap or groove 28 therebetween. The C-fold enables the second member 20 to flex thereby allowing the absorbent article 10 to conform and stay in intimate contact with a user's body, approximate the pudendum. It is a known fact, that if an absorbent article can be kept in constant contact with the body, that the likelihood of leakage is greatly minimized. Even though FIG. 1 shows a gap 28, it should be noted that the two edges 24 and 26 can slightly overlap one another or even abut one another, and still accomplish the same function as when they are spaced slightly apart. Preferably, the gap 28 can range between 0 to about 0.375 inches (about 10 mm).

When the gap 28 is present, an added feature is provided in that body fluid, present in the first member 18, has a direct route to the third member 22, which is located within the C-folded second member 20. This unobstructive pathway is especially useful when the body fluid is menses, because there is provided a clear path to allow the movement of the viscous fluid from the first member 18 down into the third member 22. A pathway which allows for rapid penetration of the body fluid into the center of the absorbent 16, is highly advantageous in keeping the cover 12 dry and providing for a no leak product.

The third member 22 is positioned within the C-folded second member 20 and has a greater wicking capacity than the second member 20. Preferably, the third member 22 will have a wicking capacity, even greater than the first member 18. The third member 22 can consist of one or more layers of tissue, a folded tissue or a meltblown material which exhibits excellent fluid distribution properties. As shown in FIG. 1, an E-folded, wet-laid and through-dried creped tissue works well in that, it is easy to manufacture and fold. The tissue can be formed from hardwood and/or softwood fibers. The tissue has a fine pore structure and provides an excellent wicking capacity, especially for menses. The third member 22 can have a width approximately equal to, less than or greater than the width of the first member 18. Practically speaking, the third member 22 can have a width ranging from between about 0.75 to about 2.25 inches (about 19 mm to about 76.2 mm). It should be noted that the third member 22 can have a width equal to the width of the second member 20 if desired. The length of the third member 22 can range from between about 5 to about 12 inches (about 127 mm to about 304 mm). It should be noted that for an article larger than a sanitary napkin, the size of the third member 22 can be proportionally sized. The length of the third member 22, can be equal to or less than the length of the second member 20, preferably slightly less than the second member 20.

The first absorbent member 18 can serve as a fluid distribution member to allow the body fluid to be distributed in a controlled manner along the length of the absorbent article 10. The second member 20 initially transfers fluid from the first member 18 into the third member 22. The third member 22 then wicks the fluid along its length and width before releasing the fluid to the second member 20. Therefore, the third member 22 can become completely saturated before the fluid is taken up by the second member 20. This action provides a good in-use visual signal to the user that the fluid is staying in the center of the absorbent article 10 thereby reinforcing the in-use visual signal initially conveyed to the user. The fluid is therefore being wicked uniformly along both the first and third members, 18 and 22 respectively, keeping the fluid in the center of the absorbent article 10. When the user notices that the wider, second member 20 is discolored with body fluid, she knows that it is approaching time to change the absorbent article 10.

The absorbent article 10 also contains a wet resilient member 30, which is positioned between the second member 20 and the liquid-impermeable baffle 14. The wet resilient member 30 can be a closed cell, polyethylene foam presently commercially sold by Sealed Air Corporation, 7110 Santa Fe Drive, Hodgkins, Ill. 60525. The foam is sold as Cell-Aire ®, CA-30 having a thickness of about 1/32 of an inch (about 0.8 mm), with a density of 1.2 pounds per cubic foot, a width of 60 inches, and on rolls having a linear length of 2000 feet (615 meters). Another polyethylene foam that is also suitable for the wet resilient member 30, is sold by Ametek Microfoam Division, Brandwine Four Building, Routes 1 and 202, Chadds Ford, Pa. 19317.

The wet resilient member 30 serves to resist bunching and twisting of the absorbent article 10 during use. By wet resilient is meant that the member 30 is resilient even when wetted by body fluid. The wet resilient member 30 has a length and a width which can be coterminous with the length and width of the cover 12 and/or the baffle 14. The wet resilient member 30 should have a width equal to or greater than the width of the absorbent 16 and a length equal to or greater than the length of the absorbent 16. The wet resilient member 30 resists bunching and twisting of the absorbent article 10 and therefore cooperates with the gap 28 in keeping the absorbent article 10 in intimate contact with the user's body.

Physically attached to an exterior surface 32 of the baffle 14, are two longitudinally extending strips of garment attachment adhesive 34 and 36. It should be noted that one wide strip, three or more narrow strips, or a spray pattern of adhesive can also be used. The garment attachment adhesive is commercially available from National Starch and Chemical Company, located at 10 Finderne Ave., Bridgewater, N.J. 08807. The garment adhesive strips 34 and 36 are used to secure the absorbent article 10 to the inside of the crotch portion of an undergarment, when the absorbent article 10 is a catamenial product. If the absorbent article 10 is a diaper or a training pant, the garment adhesive strip 34 and 36 may not be needed. The garment adhesive strips 34 and 36 serve to properly align the absorbent article 10 over the vaginal opening.

A releasable peel strip 38 is attached to the garment adhesive strips 34 and 36 and serves to prevent the adhesive from becoming contaminated prior to attachment to an undergarment. The peel strip 38 can be a white Kraft paper, coated on one side, so that it can be released from a hot melt adhesive, such as the garment adhesive strips 34 and 36. The peel strip 38 is designed to be removed ultimately by the consumer just prior to placement of the absorbent article 10 in the undergarment.

Tests were conducted to determine the wicking capacities of the various materials of different absorbent articles, specifically sanitary napkins. The test procedure determined the wicking capacity of the various materials using a dye solution which was dispensed at a flow rate of $3 \pm 0.5$ milliliters (ml)/30 seconds. Measurements were taken at two different times, at 30 seconds to establish an initial insult and at 5 minutes after initial insult. The equipment and materials needed for the test are as follows:

1. an automated pump capable of dispensing $3 \pm 0.5$ ml in 30 seconds. An automated Cole Parmer-Masterflex ® pump, available from Cole-Parmer Instrument Company, Chicago, Ill. 60648 works well;
2. a 1,000 ml capacity Pyrex graduate with 10 ml graduation;
3. a ring stand—15 inches (381 mm) high;
4. a needle, having a ⅛ inch (3 mm) tip, mounted to the ring stand;
5. Masterflex Tygon tubing, #14, available from Cole-Parmer Instrument Company;
6. 40 ml of a dye solution formed from mixing 16.7 grams of blue dye, No. 1 powder, available from the Warner-Jenkinson Division of Universal Foods Corporation located at 2526 Baldwin Street, P O Box 14538, St. Louis, Mo. 63178-4538, which has been mixed with 1,000 ml of distilled water;
7. 900 ml of distilled water;
8. a stopwatch, readable to 0.1 second; and
9. a metric ruler.

Before starting the test, 40 ml of the dye solution is gently swirled with 900 ml of distilled water in the 1000 ml capacity pyrex graduate.

The samples to be tested should be conditioned as follows: first, each sample should be removed from a protective package, if the sample is retained in a package. Each sample should then be held at a temperature of $73° F. \pm 1° F.$ and at a relative humidity of $50\% \pm 2\%$ for at least 2 hours. After being conditioned, a 2 by 6 inch (52 mm×152 mm) specimen is cut from the center of each sample. The longer dimension corresponds to the length of the article from which it is cut.

The test procedure for each specimen is as follows: each 2 by 6 inch specimen is laid on a table with it's body side surface facing up. The tip of the needle is centered over the specimen. The switch which controls the flow of the dye solution from the pump is turned on to allow the dye solution to flow onto the center of the specimen. The stopwatch is started as soon as the dye solution drips onto the specimen. At 30 seconds, the switch to the pump is turned off and the stopwatch is simultaneously stopped. This time period represents what is referred to in the Tables as the "initial insult" and the amount of fluid dispensed should be 3 ml. As quickly as possible, the cover is removed from the specimen. The length and width of the fluid stain on the first and second members, and each additional member if one is present, is measured with the metric ruler. Each member is carefully peeled apart from the adjacent member in order to measure the fluid stain. This measurement is denoted and recorded and represents the initial insult of the dye solution. All of the members and the cover are then returned to their original position and the stopwatch is started. Five minutes thereafter the stopwatch is stopped. As quickly as possible, the cover is removed from the specimen. The length and width of the fluid stain on the absorbent members, as described above, are measured and recorded. These measurements are denoted and recorded as the "5 minute after insult" reading. This is the final measurement.

The data appearing in Table 1 below was obtained using the above described test procedure. Four commercially available sanitary napkins were tested along with two prototypes of the present invention. The two prototypes are labelled as Prototypes 1 and 2. One can see from the data that after 5 minutes from initial insult, the length of the fluid stain in either the first or the third absorbent members, 18 and 22 respectively, for Prototypes 1 and 2 (110 mm, 129 mm and 110 mm, 115 mm) were much longer than the fluid stain length of any member of the commercial products. The highest value for any of the commercially tested products was 95 mm, see (KUT 2nd member). The first and third absorbent members (18 and 22, respectively) in Prototypes 1 and 2 clearly had a greater wicking capacity than the second absorbent member 20.

greater wicking members to wick the body fluid much more efficiently than the lowest wicking member.

TABLE 1

WICKING CAPACITY
(n = 1)
(all measurements in mm)

| Product | Absorbent Member | Composite Size w × l | Sq. Area | stain width after 3 ml insult | stain length after 3 ml insult | stain width 5 minutes after insult | stain length 5 minutes after insult |
|---|---|---|---|---|---|---|---|
| AUM | 1-top member | 52 × 152 | 7904 | 45 | 45 | 50 | 50 |
| | 2-inner member | 52 × 152 | 7904 | 52 | 60 | 52 | 70 |
| SFUP | 1-top member | 52 × 152 | 7904 | 54 | 55 | 54 | 60 |
| | 2-Sph member | 52 × 152 | 7904 | 54 | 62 | 54 | 66 |
| PROTOTYPE 1 | 1-Meltblown | 32 × 152 | 4864 | 32 | 83 | 32 | 110 |
| | 2-Airtex ® | 52 × 152 | 7904 | 47 | 60 | 49 | 65 |
| | 3-Tissue | 41 × 152 | 6232 | 41 | 98 | 41 | 129 |
| PROTOTYPE 2 | 1-Meltblown | 32 × 152 | 4862 | 32 | 70 | 32 | 110 |
| | 2-Coform | 52 × 152 | 7904 | 41 | 50 | 50 | 55 |
| | 3-Tissue | 41 × 152 | 6232 | 41 | 79 | 41 | 115 |
| KUT | 1-Mod. Meltblown | 32 × 152 | 4844 | 32 | 55 | 32 | 55 |
| | 2-Tissue | 52 × 152 | 7904 | 52 | 70 | 52 | 95 |
| | 3-inner member | 32 × 152 | 4864 | 32 | 50 | 32 | 52 |
| NF Maxi | 1-Meltblown | 52 × 152 | 7904 | 32 | 38 | 32 | 40 |
| | 2-Fluff | 52 × 152 | 7904 | 22 | 24 | 25 | 30 |
| | 3-Emb. Fluff | 52 × 152 | 7904 | 30 | 32 | 40 | 60 |

Note: Some swelling occurred in some of the composite members resulting in stain sizes slightly larger than the cut size.

Products
AUM         Always Ultra Maxi - commercial product sold by Procter & Gamble Company
SFUP        Stayfree Ultra Plus - commercial product sold by Johnson & Johnson
PROTOTYPE 1 Ultra Thin prototype (FIG. 1)
PROTOTYPE 2 Ultra Thin Prototype - same as Prototype 1 except Coform replaces Airtex
KUT         Kotex Ultra Thin - commercial product sold by Kimberly-Clark Corporation
NF Maxi     New Freedom Maxi - commercial product sold by Kimberly-Clark Corporation Abbreviations:
Top Member =    Top member above inner member
Inner Member =  Wrapper containing superabsorbent material
Sph Member =    An absorbent member containing Sphagnum
Airtex ® =      Airtex ® 395 mfg. by James River Corporation
Tissue =        Saint Catherine's tissue 32 gsm. mfg. by Kimberly-Clark Corporation
Coform =        60% polypropylene polymer blended with 40% pulp, 100 gsm., mfg. by Kimberly-Clark Corporation
Mod MB =        Modified meltblown 60 gsm., macro pores mfg. by Kimberly-Clark Corporation
MB =            Standard meltblown 60 gsm., micro pores mfg. by Kimberly-Clark Corporation
Fluff =         Weyerhauser roll fluff pulp, NF 105.
Emb. Fluff =    Fluff that has an embossing pattern formed thereon.

Table 2 below shows the ratios of fluid stain length of two adjacent absorbent members in a sanitary napkin for the four commercial products and the two prototypes identified in Table 1. The ratio was determined by dividing the length of the fluid stain in the absorbent member having the greater wicking capacity by the length of the fluid stain in the absorbent member having the lower wicking capacity. When the product contained three absorbent members (see Prototypes 1 and 2, KUT, and NF Maxi), the length of the fluid stain for each of the two absorbent members having the greater wicking capacity was divided by the length of the fluid stain in the absorbent member having the lowest wicking capacity.

The ratios in Table 2 show that the stain length ratios 5 minutes after initial insult were 1.7, 2.0 and 2.0, 2.1, for Prototypes 1 and 2, respectively. These values are a representation of the relationship of the wicking capacity of the greater wicking members to the lowest wicking member. A larger value indicates that the difference of wicking is more pronounced between the members. Another way of stating this is to say that the two greater wicking members have a wicking capacity which is significantly greater than the wicking capacity of the lowest wicking member. This feature enables the One will notice that in Table 2, the commercial products contained ratios between 1.1 and 2.0. The KUT commercial product, which has a ratio greater than 1.7, has a lowest wicking member which is narrower than the greater wicking members. This is opposite from the construction of the present invention and could lead to premature side leakage. The NF Maxi product, which also has a ratio greater than 1.7, is also outside of the present invention for reasons which will be explained below.

TABLE 2

STAIN LENGTH RATIOS
(n = 1)

| Product | Ratio of Member | stain length ratio after 3 ml insult | stain length ratio 5 min. after insult |
|---|---|---|---|
| AUM | Member (2): Member (1) | 1.3 | 1.4 |
| SFUP | Member (2): Member (1) | 1.1 | 1.1 |
| PROTOTYPE 1 | Member (1): Member (2) | 1.4 | 1.7 |
| | Member (3): Member (2) | 1.6 | 2.0 |
| PROTOTYPE 2 | Member (1): Member (2) | 1.4 | 2.0 |
| | Member (3): Member (2) | 1.6 | 2.1 |
| KUT | Member (1): Member (3) | 1.1 | 1.1 |
| | Member (2): Member (3) | 1.4 | 1.8 |
| NF Maxi | Member (1): Member (2) | 1.6 | 1.3 |

TABLE 2-continued

STAIN LENGTH RATIOS
(n = 1)

| Product | Ratio of Member | stain length ratio after 3 ml insult | stain length ratio 5 min. after insult |
|---|---|---|---|
| | Member (3): Member (2) | 1.3 | 2.0 |

In Table 3, the wicking capacity in terms of fluid stain length of the four commercial products and the two prototypes described in Tables 1 and 2 are given. The fluid stain length after the initial "3 ml" insult (at 30 seconds) and "5 minutes after initial insult" are listed. The values in the right hand column, "Stain length 5 minutes after insult", show that for the two prototypes, the fluid stain has progressed more than 76 mm (110 mm, 129 mm, and 110 mm, 115 mm respectively). In fact, the fluid stain length in the high wicking member exceeded 99 mm for both prototypes. In the commercial products, the fluid stain length was 70 mm or below in every product except KUT which measured 95 mm. These fluid stain lengths further support the fact that the first and third absorbent members in this invention have a greater wicking capacity than the second member. The combination of ratio of fluid stain length of the greatest wicking members divided by the fluid stain length of the lowest wicking member being greater than 1.7 along with the fluid stain being at least 76 mm, and preferably at least 99 mm, produces an unexpected result that enables the present invention to function much better than any of the tested products. It should be noted that the time period to determine the stain lengths is at 5 minutes after initial insult of 3 ml. The NF Maxi commercial product has a fluid stain length of 60 mm in the greatest wicking member, well below 76 mm. Therefore, even though the wicking ratio is fairly high, the fluid stain length of the high wicking member is showing that the fluid is not well distributed along the greatest wicking member and is therefore outside this present invention.

TABLE 3

WICKING CAPACITY STAIN LENGTH
Stain Length on Absorbent Members
(n = 1)
(all measurements in mm)

| Product | Absorbent Member | stain length after 3 ml insult | stain length 5 min. after insult |
|---|---|---|---|
| AUM | 1st member | 45 | 50 |
| | 2nd member | 60 | 70 |
| SFUP | 1st member | 55 | 60 |
| | 2nd member | 62 | 66 |
| PROTOTYPE 1 | 1st member | 83 | 110 |
| | 2nd member | 60 | 65 |
| | 3rd member | 98 | 129 |
| PROTOTYPE 2 | 1st member | 70 | 110 |
| | 2nd member | 50 | 55 |
| | 3rd member | 79 | 115 |
| KUT | 1st member | 55 | 55 |
| | 2nd member | 70 | 95 |
| | 3rd member | 50 | 52 |
| NF Maxi | 1st member | 38 | 40 |
| | 2nd member | 24 | 30 |
| | 3rd member | 32 | 60 |

Figure 2:
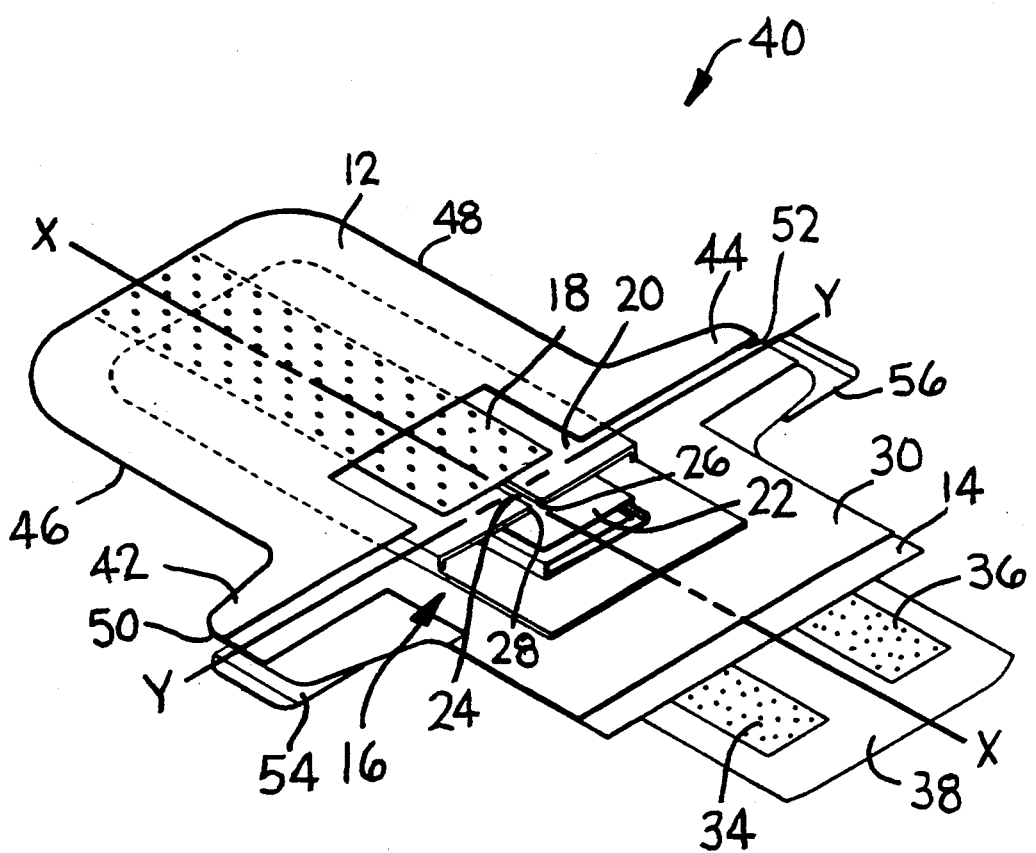
FIG. 2 is a cut away, perspective view of an absorbent article, similar to that shown in FIG. 1 and further including a pair of outwardly extending side tabs.

Referring to FIG. 2, an absorbent article 40 is shown which is similar to that depicted in FIG. 1 except that it contains a pair of tabs 42 and 44 which are capable of being folded under the crotch portion of an undergarment. Each tab, 42 and 44 respectively, extends outward from a longitudinal side edge, 46 and 48 respectively, of the absorbent article 40. The tabs 42 and 44 can have any desired configuration, but a rectangular or trapezoidal configuration works well. When a trapezoidal shape is used, the sides of the tabs 42 and 44 can taper inward as they progress toward a distal end, 50 and 52 respectively, at an angle of about 1 degree to about 25 degrees. A preferred angle is about 12 degrees. The taper is measured relative to a central transverse axis Y—Y of the absorbent article 40.

The tabs 42 and 44 can have a surface area of about 1.2 in.$^2$ (7.7 cm$^2$). The tabs 42 and 44 have a length measured parallel to the longitudinal axis X—X of the absorbent article 40, and a width, measured parallel to the transverse axis Y—Y of the absorbent article 40. The length of each tab 42 and 44 can be measured from the center of a radius, formed on one side of the tab to the center of a radius formed on an opposite side of the tab. The radii join the sides of the tabs 42 and 44 to the longitudinal side edges 46 and 48 of the absorbent article 40. The length of each tab 42 and 44 should be between about 0.75 to about 2.0 inches (about 19 mm to about 51 mm), preferably about 1.5 inches (about 38 mm). The width of each tab 42 and 44 can be between about 0.5 to about 1.5 inches (about 13 mm to about 38 mm), preferably about 1 inch (about 25.4 mm).

It should be noted that the size, shape and thickness of the tabs 42 and 44 can vary depending upon the size and configuration of the absorbent article they are attached to.

The tabs 42 and 44 are constructed of the cover 12, the baffle 14 and the wet resilient member 30. Therefore, the tabs 42 and 44 are thinner and have a Gurley stiffness which is less than that of the absorbent 16. Each tab 42 and 44 also contains a patch or strip of garment adhesive (not shown) attached to the baffle side of each tab 42 and 44 which is covered by a releasable peel strip, 54 and 56 respectively. The garment adhesive should cover an area of at least 0.5 square inches (about 323 mm$^2$) of each tab 42 and 44, and preferably, at least 50% of each tab 42 and 44. The particular shape and configuration of the adhesive; can vary. A garment adhesive which works well is adhesive NS 34-5516 which is commercially available from National Starch Company, located at 10 Finderne Ave., Bridgewater, N.J. 08807.

The tabs 42 and 44 should have a Gurley stiffness in the range of between about 50 milligrams (mg) to about 150 mg, preferably about 77 mg to about 115 mg when the peel strip is removed to provide optimum comfort and drapability. For the range of about 50 mg to about 150 mg of stiffness, the tabs 42 and 44 should have a thickness of greater than about 0.5 mm, preferably about 0.7 mm to about 1.5 mm, and most preferably about 1.1 mm to about 1.2 mm when the peel strip is removed, see values for Prototype 1 in Table 4.

GURLEY STIFFNESS

To test the Gurley stiffness of a tab on an absorbent article containing a peel strip, one should use a Gurley Digital Stiffness Tester, Model 4171-d. Five samples of each article should be tested. At least one tab on each article must be tested. The articles are removed from any pouch that they may be contained in and are unfolded. The articles are then conditioned by holding them at a temperature of 73° F.±1° and at a relative humidity of 50%±2% for at least 2 hours before testing. A 12.7 mm×25.4 mm sample is then cut from the center of one tab per article. It should be noted that if the article contains a single peel strip on only one tab, then the tab without the peel strip should be used for this portion of the test. It is also important to avoid testing those areas of a tab which contain Velcro ® or other types of hook and loop fasteners. The articles should be carefully handled to avoid affecting the stiffness of the sample.

The Gurley stiffness tester should be calibrated before use. One should follow the instruction manual of the Gurley stiffness tester and stay within 5% variation using a 50.8 mm wide by 25.4 mm long pre-calibrated Brass Calibration Strip. This is done to ensure that the "Vane" pendulum is swinging according to specification against a known material (i.e. a brass strip). The electronics of the tester should be calibrated as stated in the instruction manual. In setting up the Gurley stiffness tester, one will have to attach the required weight and adjust the leveling screw, until the level's bubble is centered and the pendulum's pointer is indicating zero. The switches should be set for specified weight, specified weight position, width (0.5 inches) and length (1 inch). The test procedure involves the following steps:
1) The sample is centered over the pendulum such that exactly 6.4 mm (0.25 inches) overlaps the top of the pendulum and exactly 6.4 mm (0.25 inches) will be held in the jaws.
2) The reading should be checked to make sure it is between 2 and 6 on the scale. If not, adjust the weight and reset the switch as needed. The sample should be positioned in close contact with the pendulum vane before applying a force. This will avoid oscillation in the early stages.
3) The System Reset button is then pressed. The display must read 00-000.
4) The operator will then press the motor-direction switch to cause the clamp arm to press the sample against the pendulum.
5) Step 4 is repeated in the opposite direction to establish both a left scale reading, a right scale reading and an average reading.
6) The average scale reading is then recorded.
7) The select button is then pressed to attain milligram calculation and record the value.
8) Steps 1–7 are repeated for each sample.

TAB THICKNESS

To test for the thickness of a tab on an absorbent article after any peel strip is removed, one would use an Ames Bulk Tester with a dial indicator, Model No. 482. At least one tab on each article must be tested. Five samples of each article should be tested. The articles are removed from any pouch that they may be contained in and are unfolded. The articles are then conditioned by holding them at a temperature of 73° F.±1° and at a relative humidity of 50%±2% for at least 2 hours before testing. The center of the non-adhesive side of each tab is then marked using a marker and a ruler. The comparator gauge on the Ames Bulk Tester is zeroed. An 80.0 grams stainless steel weight is placed on the spindle extending above the comparator dial. The circular aluminum comparator foot (having a contact surface of 5.16 cm$^2$ and having a weight of 10 g) on the Ames Bulk Tester is then moved to its upper limit and a sample is placed on the base of the tester with the garment adhesives facing down. This position allows the foot of the tester to be lower onto the center of the tab. The lever on the tester is then gently released to lower the comparator foot onto the sample. The dial is read 30 seconds after the foot comes in contact with the material of which the tab is constructed. The measurement is recorded in inches, as indicated on the dial. The measurement can be converted to millimeters by multiplying the value by 25.4. The number should be recorded to two places to the right of the decimal point. The foot is then raised and the sample is removed so that subsequent samples can be tested. It is important that the base of the tester be cleaned after each sample.

To test tabs without the peel strip, the peel strip is removed from the tab and the garment adhesive is dusted with talc or corn starch.

Measurements on the present absorbent article 10 and commercially available sanitary products were made using the above-identified test procedures for Gurley stiffness and thickness. Five samples of each product were tested using one tab from each product. The data is summarized in Table 4 below.

TABLE 4

| PRODUCT | TAB GURLEY STIFFNESS (mg) without peel | TAB THICKNESS (mm) without peel |
|---|---|---|
| Prototype 1 | 77–115 | 1.1–1.2 |
| Kotex ® Lightdays ® WrapAround ™ Pantiliner | 177–300 | 1.7–1.9 |
| Libresse ® | 9–20 | .03–.36 |
| Always ® Ultra Plus | 3–13 | .02–.51 |
| Always ® Plus Long Thin Maxi Pad with Wings | 0–14 | .02–.51 |
| Stay Free ® Ultra Plus Maxi | .5–1.9 | .33–.38 |
| Kao Night Safe | 3–11 | .20–.25 |

The data indicates that the tabs 42 and 44 have a Gurley stiffness which falls within a unique range, higher than the Gurley stiffness of most of the prior art products, and lower than the Gurley stiffness of the WrapAround ® pantiliner. This unique range of Gurley stiffness has been found to be the most suitable for the function of the tabs. Tabs that are in the range of stiffness of the WrapAround ® pantiliner have been found to suffer from a lack of conformability. They have a tendency to lose their attachment to the undergarment during use in wear conditions. This stiffness range is also not optimum for comfort. For optimum performance and comfort, the tabs should have a Gurley stiffness of less than about 150 mg.

The vast majority of the prior art tabs or wings have a Gurley stiffness that is less than about 50 mg. In fact, those tested in Table 4 have a Gurley stiffness of less than 20 mg. This is in line with prior teachings that the more flexible the wings or tabs, the better they will perform (e.g. U.S. Pat. No. 4,608,047, issued to Mattingly). It has been found, however, that prior art made with this teaching in mind suffers from several serious deficiencies. First, when the peel strip is removed from the adhesive, just prior to applying the article to an undergarment, tabs that are too flexible will droop and adhere to the bottom of the absorbent article, or to each other. This is very inconvenient for the user. Second, in use, these highly flexible tabs or wings will have a tendency to bunch and distort. This can be a functional problem, in that the bunched tabs will not do their job of holding the article in place. The bunching is also a comfort problem, in that the wrinkles resulting from bunching are uncomfortable.

It has been found that when the tabs have a Gurley stiffness of about 50 mg or above they are sufficiently stiff that they do not stick to the absorbent article upon removal of the peel strip. Furthermore, the tabs exhibit greatly improved resistance to in use bunching relative to prior art tabs that are more flexible.

It is important when using tabs that have a Gurley stiffness greater than about 50 mg that the tabs also have a thickness greater than about 0.5 mm. This will insure that the tabs are comfortable. Tabs stiffer than about 50 mg and thinner than about 0.5 mm will present a side edge that can feel sharp to the user, and therefore can cause discomfort.

Figure 3:
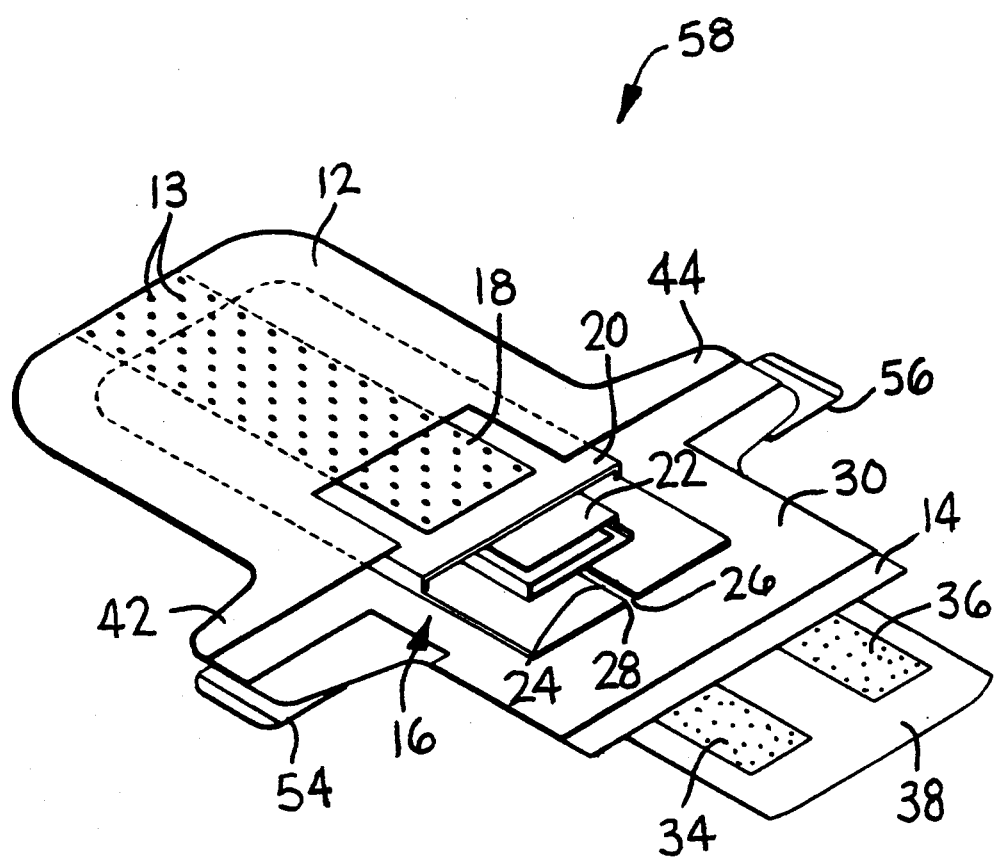
FIG. 3 is a cut away, perspective view of an absorbent article, having three absorbent members wherein the second member is C-folded about the third member and has a longitudinal gap which faces away from the first member.

Referring to FIG. 3, an absorbent article 58 is shown which is similar to that depicted in FIG. 2, except that the second member 20 is C-folded such that the gap or groove 28 faces downward towards the baffle 14. Such an embodiment may be easier to manufacture on some equipment.

Figure 4:
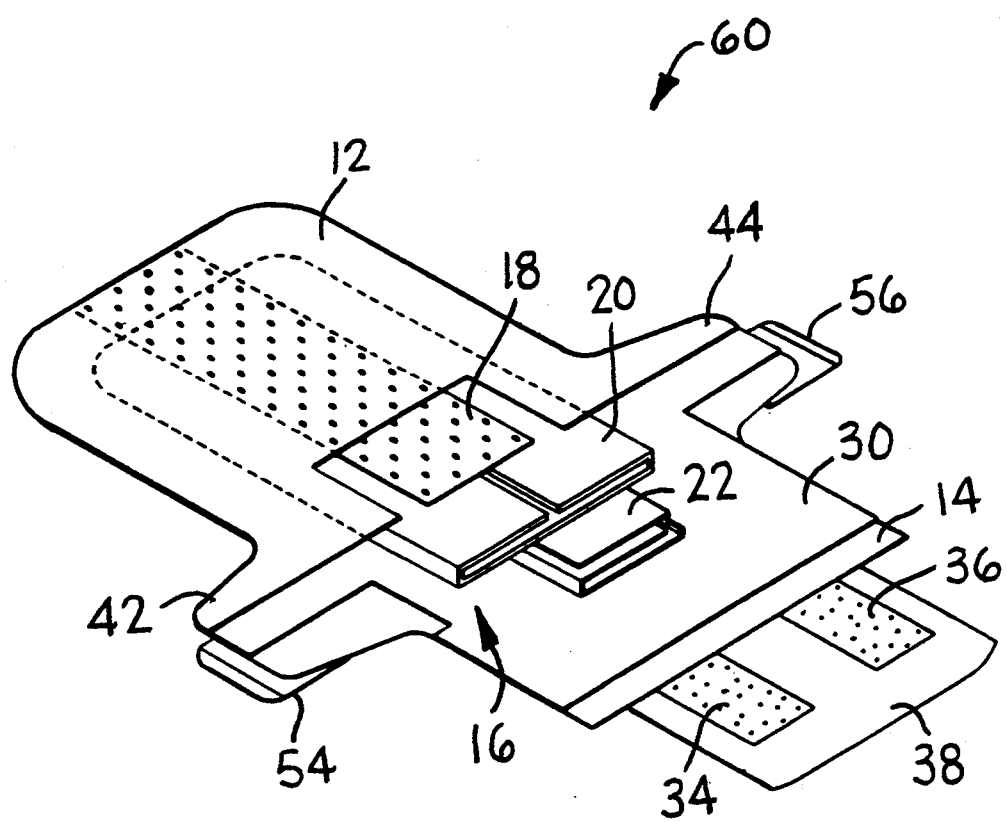
FIG. 4 is a cut away, perspective view of an absorbent article, having three absorbent members wherein the second member is C-folded and has a longitudinal gap which faces the first member and the third member is positioned below the second member.

Referring to FIG. 4, an absorbent article 60 is shown which is similar to that depicted in FIG. 2 except that the third member 22 is positioned below the second member 20. In this arrangement, it is possible to make both the second and third members, 20 and 22 respectively, of the same width. By positioning the third member 22 below the second member 20 instead of within the C-fold, the absorbent article 60 may be easier to manufacture.

Figure 5:
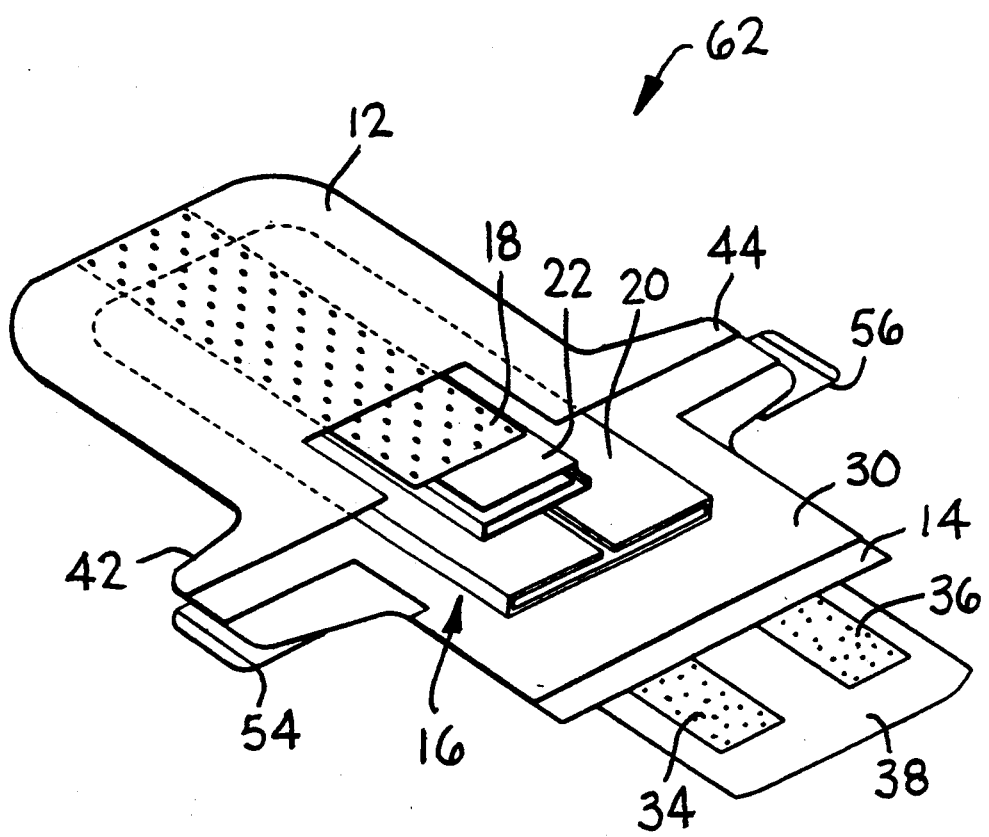
FIG. 5 is a cut away, perspective view of an absorbent article, having three absorbent members wherein the wider second member is positioned below both the first and third members.

Referring to FIG. 5, an absorbent article 62 is shown which is similar to that depicted in FIG. 2, except that the third member 22 is positioned above the second member 20. In this arrangement, it is possible to make both the second and third members, 20 and 22 respectively, of the same width. By positioning the third member 22 above the second member 20 instead of within the C-fold, the absorbent article 60 may be easier to manufacture.

Figure 6:
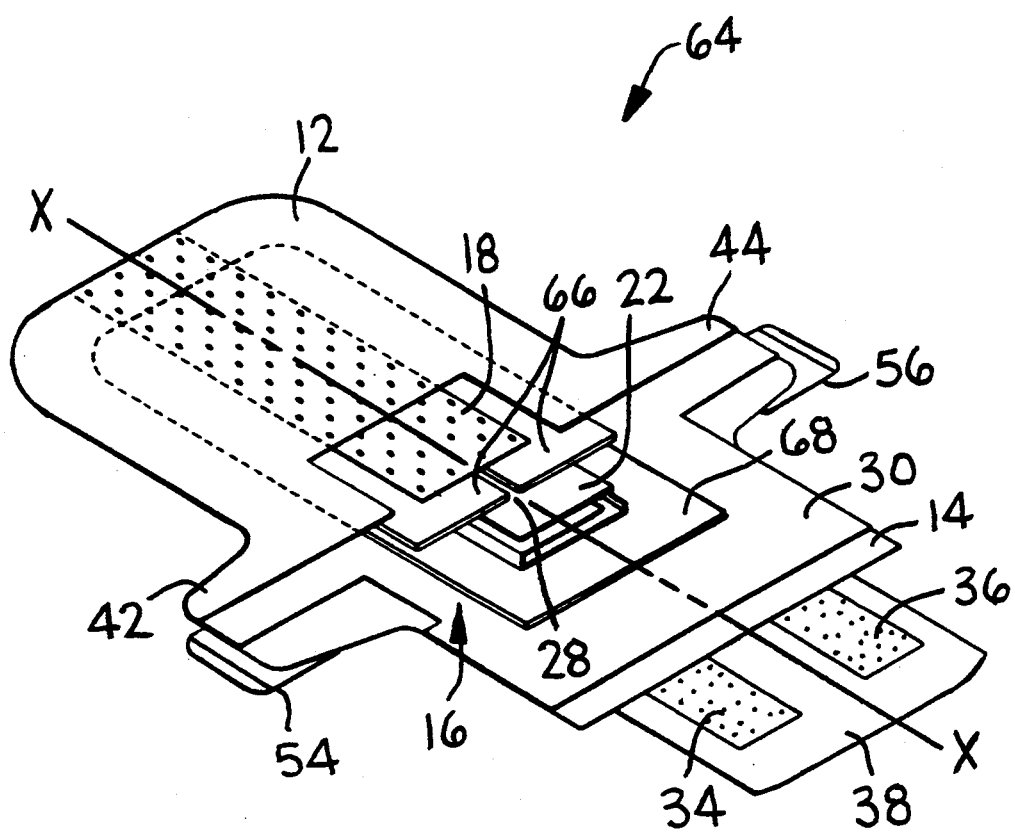
FIG. 6 is a cut away, perspective view of an absorbent article, having an absorbent constructed of four separate and distinct members.

Referring to FIG. 6, an absorbent article 64 is shown which is similar to that depicted in FIG. 2, except that the second member 20 is not C-folded but instead consist of two separate members 66 and 68. The member 66 is positioned above the third member 22 while the member 68 is positioned below the third member 22. In this embodiment, the members 66 and 68 would be made out of the same material and would have the same wicking capacity. However, if one desired to change the material or wicking properties of the member 68, this could easily be done. The gap or groove 28 would still be present in the member 66 to facilitate movement of body fluid downward into the third member 22. The gap 28 can be formed by constructing the member 66 out of two separate strips of material and laying them parallel to one another and slightly spaced apart. Another way to obtain the gap 28 is to form a slit in the member 66 only along a portion of its length. The gap 28 should be in alignment with the longitudinal central axis X—X of the absorbent article 64.

While the invention has been described in conjunction with several specific embodiments, it is to be understood that many alternatives, modifications and variations will be apparent to those skilled in the art in light of the aforegoing description. Accordingly, this invention is intended to embrace all such alternatives, modifications and variations which fall within the spirit and scope of the appended claims.

We claim:

1. An absorbent article having a longitudinal axis comprising first, second and third vertically aligned members, said second and third members being positioned below said first member, said first member having a wicking capacity along said longitudinal axis, said second member having a lower wicking capacity along said longitudinal axis than said first member, and said third member having a greater wicking capacity along said longitudinal axis than said second member, said first member having a width and said second member having a width greater than the width of said first member, and said second member having a basis weight of less than about 300 gsm.

2. The absorbent article of claim 1 wherein said third member is positioned within said second member.

3. The absorbent article of claim 1 wherein said third member has a greater wicking capacity along said longitudinal axis than said first member.

4. The absorbent article of claim 1 wherein said third member is wider than said first member.

5. The absorbent article of claim 1 wherein said first member is meltblown.

6. The absorbent article of claim I wherein said second member is coform.

7. The absorbent article of claim I wherein said second member is an air-laid fabric.

8. The absorbent article of claim 1 wherein said third member is a through-air dried, creped tissue.

9. The absorbent article of claim 1 wherein a fourth member is positioned below said third member, said fourth member having a lower wicking capacity along said longitudinal axis than either said first or third members.

10. An absorbent article having a longitudinal axis comprising first, second and third vertically aligned members, said second member positioned below said first member and said third member positioned within said second member, said first member having a wicking capacity along said longitudinal axis, said second member having a lower wicking capacity along said longitudinal axis than said first member, and said third member having a greater wicking capacity along said longitudinal axis than said second member, said first member having a width and said second member having a width greater than the width of said first member, said third member having a width slightly less than the width of said second member, and said second member having a basis weight of less than about 300 gsm.

11. The absorbent article of claim 10 wherein said first and third members have approximately the same width.

12. The absorbent article of claim 10 wherein said third member has a width greater than said first member.

13. An absorbent article having a longitudinal axis comprising:
 a) a liquid-permeable cover;
 b) a liquid-impermeable baffle; and
 c) an absorbent enclosed by said cover and said baffle, said absorbent including first, second and third members, said first member positioned immediately below said cover, said second member positioned below said first member and said third member positioned within said second member, said first member having a wicking capacity along said longitudinal axis, said second member having a lower wicking capacity along said longitudinal axis than said first member, and said third member having a greater wicking capacity along said longitudinal axis than said second member, said first member having a width and second member having a width greater than the width of first member, and said second member having a basis weight of less than about 300 gsm.

14. The absorbent article of claim 13 wherein said second member is C-folded which enables said second member to flex thereby permitting said absorbent article to conform to a user's body.

15. The absorbent article of claim 13 wherein said third member has a greater wicking capacity along said longitudinal axis than said first member.

16. The absorbent article of claim 13 wherein said absorbent has a thickness of less than about 7 millimeters.

17. The absorbent article of claim 16 wherein said absorbent has a thickness of less than about 5 millimeters.

18. The absorbent article of claim 13 wherein a wet resilient member is positioned between said absorbent and said baffle which offers resistance to bunching of said absorbent article.

19. The absorbent article of claim 18 wherein said wet resilient member is a polyethylene foam.

20. An absorbent article having a longitudinal axis comprising:
 a) a liquid-permeable cover;
 b) a liquid-impermeable baffle;
 c) an absorbent enclosed by said cover and said baffle, said absorbent including first, second and third vertically aligned members, said first member positioned immediately below said cover and aligned along said longitudinal axis, said first member having a wicking capacity along said longitudinal axis, said second member positioned below said first member and having a lower wicking capacity along said longitudinal axis than said first member, said first member having a width and said second member having a width greater than the width of said first member, said second member being C-folded and having two oppositely aligned edges which are spaced apart to form a gap therebetween, said C-fold enabling said second member to flex thereby allowing said absorbent article to conform to a user's body, and said third member positioned within said second member and having a greater wicking capacity than said second member; and
 d) a wet resilient member positioned between said absorbent and said baffle which offers resistance to bunching of said absorbent article.

21. The absorbent article of claim 20 wherein said first member is a narrow strip aligned along said central longitudinal axis of said absorbent article.

22. The absorbent article of claim 20 wherein said first member is meltblown.

23. The absorbent article of claim 20 wherein said second member is C-folded with said gap positioned adjacent to said first member.

24. The absorbent article of claim 20 wherein said second member is C-folded with said gap positioned adjacent to said wet resilient member.

25. The absorbent article of claim 20 wherein said cover and baffle are sized and configured to form a pair of tabs which can fold and which extend outwardly from said absorbent approximate a middle portion thereof, and said cover and baffle being sealed together about the periphery of said absorbent article.

26. The absorbent article of claim 25 wherein each of said tabs contains attachment means for securing said tab to an undergarment.

27. The absorbent article of claim 26 wherein each of said tabs has a Gurley stiffness of between about 50 mg to about 150 mg and a thickness of greater than about 0.5 mm.

28. An absorbent article having a longitudinal axis comprising first, second and third vertically aligned members, said second and third members being positioned below said first member, said first member providing an in-use visual signal that body fluid which entered said article is staying in a central portion of said article, said second and third members each having a wicking capacity along said longitudinal axis with said third member having a greater wicking capacity along said longitudinal axis than said second member, said second and third members each having a width with the width of said second member being greater than the width of said third member, and said second member having a basis weight of less than about 300 gsm.

29. The absorbent article of claim 28 wherein said first member is a layer of ink.

30. The absorbent article of claim 28 wherein said first member is a different color than said second member.

31. The absorbent article of claim 28 further including a cover and said first member is a different color than said cover.

32. The absorbent article of claim 28 further including a cover and said first member is a darker color than said cover.

33. An absorbent article having a longitudinal axis, comprising:
 a) a liquid-permeable cover;
 b) a liquid-impermeable baffle;
 c) an absorbent enclosed by said cover and said baffle, said absorbent including first, second and third vertically aligned members, said first member being a strip of meltblown material positioned immediately below said cover and aligned along said longitudinal axis, said first member having a wicking capacity along said longitudinal axis, said second member positioned below said first member and having a lower wicking capacity along said longitudinal axis than said first member, said second member being C-folded and having two oppositely aligned edges which are spaced apart to form a gap therebetween, said C-fold enabling said second member to flex thereby allowing said absorbent article to conform to a user's body, and said third member positioned within said second member and having a greater wicking capacity along said longitudinal axis than said first and second members; and
 d) a wet resilient member positioned between said absorbent and said baffle which offers resistance to bunching of said absorbent article.

34. An absorbent article having a longitudinal axis, a central transverse axis and a pair of longitudinal side edges, said absorbent article comprising:
 a) a liquid-permeable cover;
 b) a liquid-impermeable baffle having a garment-facing surface;
 c) an absorbent enclosed by said cover and said baffle, said absorbent including first, second and third vertically aligned members, said first member being a strip of meltblown material positioned immediately below said cover and aligned along said longitudinal axis, said first member having a wicking capacity along said longitudinal axis, said second member positioned below said first member and having a lower wicking capacity along said longitudinal axis than said first member, said second member being C-folded and having two oppositely aligned edges which are spaced apart to form a gap therebetween, said C-fold permitting said second member to flex thereby allowing said absorbent article to conform to a user's body, and said third member positioned within said second member and having a greater wicking capacity along said longitudinal axis than said first and second members;

d) a wet resilient member positioned between said absorbent and said baffle which offers resistance to bunching of said absorbent article;

e) a pair of tabs which can fold and which are aligned along said central transverse axis which extend laterally outward from said longitudinal side edges of said absorbent article, said tabs including said cover, said wet resilient member and said baffle;

f) adhesive means for securing said absorbent article to an undergarment, said adhesive means being present on said garment-facing surface of said baffle at a location between said longitudinal side edges and on each of said tabs; and g) release paper covering said adhesive means.

35. An absorbent article having a longitudinal axis, a central transverse axis and a pair of longitudinal side edges, said absorbent article comprising:

a) a liquid-permeable cover;

b) a liquid-impermeable baffle having a garment-facing surface;

c) an absorbent enclosed by said cover and said baffle, said absorbent including first, second and third vertically aligned members, said first member being a strip of meltblown material positioned immediately below said cover and aligned along said longitudinal axis, said first member having a wicking capacity along said longitudinal axis, said second member positioned below said first member and having a lower wicking capacity along said longitudinal axis than said first member, said second member being C-folded and having two oppositely aligned edges which are spaced apart to form a gap therebetween, said C-fold permitting said second member to flex thereby allowing said absorbent article to conform to a user's body, and said third member positioned adjacent to said second member and having a greater wicking capacity along said longitudinal axis than said first and second members;

d) a wet resilient member positioned between said absorbent and said baffle which offers resistance to bunching of said absorbent article;

e) a pair of tabs which can fold and are aligned along said central transverse axis which extend laterally outward from said longitudinal side edges of said absorbent article, said tabs including said cover, said wet resilient member and said baffle;

f) adhesive means for securing said absorbent article to an undergarment, said adhesive means being present on said garment-facing surface of said baffle at a location between said longitudinal side edges and on each of said tabs; and g) release paper covering said adhesive means.

36. An absorbent article having a longitudinal axis comprising first, second and third vertically aligned members, said second and third members being positioned below said first member, said first member providing an in-use visual signal that body fluid which entered said article is staying in a central portion of said article, said first, second and third members each having a wicking capacity along said longitudinal axis, said second member having a lower wicking capacity along said longitudinal axis than said first member and said third member having a greater wicking capacity along said longitudinal axis than said second member, and said second member having a basis weight of less than about 300 gsm.

37. An absorbent article comprising:

a) a liquid-permeable cover;

b) a liquid-impermeable baffle;

c) an absorbent positioned between said cover and said baffle, said absorbent having a pair of longitudinally extending side edges; and d) a pair of tabs extending outwardly from said longitudinal side edges, each of said tabs containing an adhesive and each of said tabs having a Gurley stiffness of between about 50 mg to about 150 mg, and each of said tabs having a thickness of greater than about 0.5 mm.

* * * * *

Adverse Decision In Interference

Patent No. 5,401,267, Laurie Couture-Dorschner, David R. King, Ann M. Nichols, Thomas H. Gilman, Valerie V. Finch, ABSORBENT ARTICLE HAVING ENHANCED WICKING CAPACITY, Interference No. 104,222, final judgment adverse to the patentees rendered September 28, 2001, as to claim 37.

*(Official Gazette March 26, 2002)*